United States Patent
Yeh et al.

(10) Patent No.: US 11,419,981 B2
(45) Date of Patent: Aug. 23, 2022

(54) PRIMING APPARATUS AND METHOD

(71) Applicant: CareFusion 303, Inc., San Diego, CA (US)

(72) Inventors: Jonathan Yeh, Diamond Bar, CA (US); Jake R. Smith, Yorba Linda, CA (US); Soon Y. Park, Cypress, CA (US); Tammy Nguyen, Irvine, CA (US)

(73) Assignee: CAREFUSION 303, INC., San Diego, CA (US)

( * ) Notice: Subject to any disclaimer, the term of this patent is extended or adjusted under 35 U.S.C. 154(b) by 105 days.

(21) Appl. No.: 16/563,416

(22) Filed: Sep. 6, 2019

(65) Prior Publication Data

US 2020/0001008 A1    Jan. 2, 2020

Related U.S. Application Data

(62) Division of application No. 14/712,634, filed on May 14, 2015, now Pat. No. 10,413,662.

(51) Int. Cl.
*A61M 5/168* (2006.01)
*A61M 5/14* (2006.01)
*A61M 5/162* (2006.01)
*A61M 39/24* (2006.01)

(52) U.S. Cl.
CPC ...... *A61M 5/16822* (2013.01); *A61M 5/1411* (2013.01); *A61M 5/162* (2013.01); *A61M 39/24* (2013.01); *A61M 2005/1402* (2013.01)

(58) Field of Classification Search
CPC ...... A61J 1/2096; A61J 1/2037; A61J 1/2089; G01F 11/10; G01F 11/26
See application file for complete search history.

(56) References Cited

U.S. PATENT DOCUMENTS

| | | | |
|---|---|---|---|
| 2,074,223 A | * | 3/1937 | Horiuchi .............. A61M 1/0011 604/4.01 |
| 2,668,533 A | | 2/1954 | Evans |
| 2,673,013 A | | 3/1954 | Hester |
| 2,812,117 A | | 11/1957 | Butkus |
| 2,852,024 A | | 9/1958 | Ryan |

(Continued)

FOREIGN PATENT DOCUMENTS

| | | |
|---|---|---|
| CN | 1950126 A | 4/2007 |
| CN | 102883763 A | 1/2013 |

(Continued)

OTHER PUBLICATIONS

Chinese Office Action for Application No. 201680027428.2, dated Dec. 31, 2019, 24 pages.

(Continued)

*Primary Examiner* — Scott J Medway
(74) *Attorney, Agent, or Firm* — Morgan, Lewis & Bockius LLP

(57) ABSTRACT

A priming system including a resilient chamber having flexible walls and a first check valve in a first fluid pathway between the resilient chamber and a fluid reservoir such that a fluid flows through the first check valve only in a direction from the fluid reservoir toward the resilient chamber and the fluid returns to the fluid reservoir through a second fluid pathway between the resilient chamber and the fluid reservoir upon compression of the walls of the resilient chamber.

16 Claims, 12 Drawing Sheets

(56) References Cited

U.S. PATENT DOCUMENTS

| | | | |
|---|---|---|---|
| 3,023,750 A | 3/1962 | Baron | |
| 3,153,414 A * | 10/1964 | Beall | A61M 5/155 222/95 |
| 3,291,151 A | 12/1966 | Loken | |
| 3,314,600 A | 4/1967 | Hadley | |
| 3,542,240 A * | 11/1970 | Solowey | A61M 5/162 222/83 |
| 3,584,770 A | 6/1971 | Taylor | |
| 3,608,550 A | 9/1971 | Stawski | |
| 3,797,521 A | 3/1974 | King | |
| 3,938,520 A | 2/1976 | Scislowicz | |
| 3,980,082 A | 9/1976 | Miller | |
| 4,038,983 A | 8/1977 | Mittleman | |
| 4,381,776 A * | 5/1983 | Latham, Jr. | A61J 1/05 128/DIG. 24 |
| 4,396,016 A | 8/1983 | Becker | |
| 4,410,321 A | 10/1983 | Pearson | |
| 4,413,990 A | 11/1983 | Mittleman | |
| 4,458,733 A | 7/1984 | Lyons | |
| 4,534,758 A | 8/1985 | Akers | |
| 4,564,054 A | 1/1986 | Gustavsson | |
| 4,600,040 A | 7/1986 | Naslund | |
| 4,673,404 A * | 6/1987 | Gustavsson | A61J 1/2096 604/411 |
| 4,857,068 A | 8/1989 | Kahn | |
| 4,951,839 A | 8/1990 | Kong | |
| 5,071,034 A | 12/1991 | Corbiere | |
| 5,195,987 A * | 3/1993 | Karpiak | A61M 5/14 604/257 |
| 5,385,545 A * | 1/1995 | Kriesel | A61K 47/6957 604/82 |
| 5,445,630 A | 8/1995 | Richmond | |
| 5,509,433 A | 4/1996 | Paradis | |
| 5,700,245 A | 12/1997 | Sancoff | |
| 5,934,510 A * | 8/1999 | Anderson | B05B 11/3002 604/218 |
| 6,474,375 B2 | 11/2002 | Spero | |
| 6,537,258 B1 | 3/2003 | Guala | |
| 6,715,520 B2 | 4/2004 | Andreasson | |
| 6,764,467 B1 | 7/2004 | Roby | |
| 7,086,431 B2 | 8/2006 | D'Antonio | |
| 7,354,427 B2 | 4/2008 | Fangrow | |
| 7,507,227 B2 | 3/2009 | Fangrow | |
| 7,510,547 B2 | 3/2009 | Fangrow | |
| 7,510,548 B2 | 3/2009 | Fangrow | |
| 7,513,895 B2 | 4/2009 | Fangrow | |
| 7,569,043 B2 | 8/2009 | Fangrow | |
| 7,645,271 B2 | 1/2010 | Fangrow | |
| 7,654,995 B2 | 2/2010 | Warren | |
| 7,658,733 B2 | 2/2010 | Fangrow | |
| 8,206,367 B2 | 6/2012 | Warren | |
| 8,211,082 B2 * | 7/2012 | Hasegawa | A61M 5/162 604/416 |
| 8,267,913 B2 | 9/2012 | Fangrow | |
| 8,506,548 B2 | 8/2013 | Okiyama | |
| 8,522,832 B2 | 9/2013 | Lopez | |
| 8,523,838 B2 * | 9/2013 | Tornqvist | F16K 17/19 604/416 |
| 8,545,446 B1 | 10/2013 | Butterfield | |
| 9,089,474 B2 | 7/2015 | Cederschiold | |
| 9,089,475 B2 | 7/2015 | Fangrow | |
| 9,132,062 B2 * | 9/2015 | Fangrow | A61J 1/201 |
| 9,205,187 B2 | 12/2015 | Butterfield | |
| 9,237,986 B2 | 1/2016 | Mansour | |
| 9,278,206 B2 | 3/2016 | Fangrow | |
| 9,440,060 B2 | 9/2016 | Fangrow | |
| 9,545,508 B2 | 1/2017 | Butterfield | |
| 9,585,812 B2 | 3/2017 | Browka | |
| 9,615,997 B2 * | 4/2017 | Fangrow | A61J 1/2096 |
| 9,662,272 B2 | 5/2017 | Warren | |
| 9,724,464 B2 | 8/2017 | Mansour | |
| 9,731,070 B2 | 8/2017 | Mansour | |
| 9,750,662 B2 | 9/2017 | Mansour | |
| 9,763,855 B2 | 9/2017 | Fangrow | |
| 10,016,339 B2 | 7/2018 | Guala | |
| 2002/0087144 A1 | 7/2002 | Zinger | |
| 2003/0070726 A1 | 4/2003 | Andreasson | |
| 2004/0215147 A1 | 10/2004 | Wessman | |
| 2005/0096627 A1 | 5/2005 | Howard | |
| 2007/0093775 A1 | 4/2007 | Daly | |
| 2007/0106244 A1 * | 5/2007 | Mosler | A61J 1/2096 604/407 |
| 2007/0244456 A1 | 10/2007 | Fangrow | |
| 2007/0244457 A1 | 10/2007 | Fangrow | |
| 2007/0244458 A1 | 10/2007 | Fangrow | |
| 2007/0244459 A1 | 10/2007 | Fangrow | |
| 2007/0244464 A1 | 10/2007 | Fangrow | |
| 2007/0244466 A1 | 10/2007 | Fangrow | |
| 2007/0270778 A9 | 11/2007 | Zinger | |
| 2008/0045919 A1 * | 2/2008 | Jakob | A61M 5/162 604/416 |
| 2008/0097315 A1 * | 4/2008 | Miner | A61M 5/1411 604/122 |
| 2008/0249498 A1 | 10/2008 | Fangrow | |
| 2008/0311007 A1 | 12/2008 | Helmerson | |
| 2008/0312634 A1 | 12/2008 | Helmerson | |
| 2009/0254031 A1 | 10/2009 | Lee | |
| 2010/0049159 A1 | 2/2010 | Fangrow | |
| 2010/0147402 A1 * | 6/2010 | Tornqvist | F16K 15/147 137/513 |
| 2011/0062703 A1 | 3/2011 | Lopez | |
| 2011/0073249 A1 | 3/2011 | Fangrow | |
| 2011/0178493 A1 | 7/2011 | Okiyama | |
| 2011/0190723 A1 | 8/2011 | Fangrow | |
| 2011/0257621 A1 | 10/2011 | Fangrow | |
| 2011/0275988 A1 * | 11/2011 | Davis | A61M 5/1411 604/82 |
| 2012/0035580 A1 | 2/2012 | Fangrow | |
| 2012/0046637 A1 | 2/2012 | Fangrow | |
| 2012/0065609 A1 | 3/2012 | Seifert | |
| 2012/0065610 A1 | 3/2012 | Seifert | |
| 2012/0157960 A1 | 6/2012 | Fangrow | |
| 2012/0179129 A1 | 7/2012 | Imai | |
| 2013/0306509 A1 | 11/2013 | Caetano | |
| 2013/0331789 A1 | 12/2013 | Butterfield | |
| 2013/0331811 A1 | 12/2013 | Butterfield | |
| 2014/0174596 A1 | 6/2014 | Lopez | |
| 2014/0299221 A1 | 10/2014 | Lopez | |
| 2015/0000787 A1 | 1/2015 | Fangrow | |
| 2015/0250680 A1 | 9/2015 | Browka | |
| 2015/0320641 A1 | 11/2015 | Fangrow | |
| 2015/0374909 A1 | 12/2015 | Mansour | |
| 2016/0101020 A1 | 4/2016 | Guala | |
| 2016/0256632 A1 | 9/2016 | Fangrow | |
| 2016/0331893 A1 | 11/2016 | Yeh | |
| 2017/0007816 A1 | 1/2017 | Mansour | |
| 2017/0079880 A1 | 3/2017 | Guala | |
| 2017/0079883 A1 | 3/2017 | Lopez | |
| 2017/0202742 A1 | 7/2017 | Cheng | |

FOREIGN PATENT DOCUMENTS

| | | | |
|---|---|---|---|
| CN | 102892459 A | 1/2013 | |
| CN | 104245015 A | 12/2014 | |
| DE | 29507730 | 9/1996 | |
| DE | 19748497 A1 * | 5/1999 | A61M 5/38 |
| JP | S60126166 A | 7/1985 | |
| JP | 2005296142 A | 10/2005 | |
| JP | 2011521753 A | 7/2011 | |
| JP | 2013525065 A | 6/2013 | |
| JP | 2014018351 A | 2/2014 | |
| JP | 2014217555 A | 11/2014 | |
| WO | WO-2015/118432 | 8/2015 | |

OTHER PUBLICATIONS

Japanese Office Action for Application No. 2017559356, dated Feb. 13, 2020, 10 pages.
European Office Action for Application No. 16724757.6, dated Apr. 22, 2020, 5 pages.

(56) References Cited

OTHER PUBLICATIONS

European Office Action for Application No. 16724757.6, dated Sep. 25, 2019, 4 pages.
International Search Report and Written Opinion for Application No. PCT/US2016/029870, dated Aug. 8, 2016, 11 pages.
Australian Examination Report for Application No. 2016261082, dated Aug. 26, 2020, 4 pages.
European Office Action for Application No. 16724757.6, dated Oct. 1, 2020, 6 pages.
Australian Examination Report for Application No. 2021200965, dated Aug. 30, 2021, 2 pages.
European Office Action for Application No. 16724757.6, dated Jun. 29, 2021, 5 pages.
Chinese Office Action for Application No. 202011094935.2, dated Dec. 24, 2021, 18 pages including translation.
Japanese Office Action for Application No. 2020-202812, dated Sep. 29, 2021, 8 pages including translation.

* cited by examiner

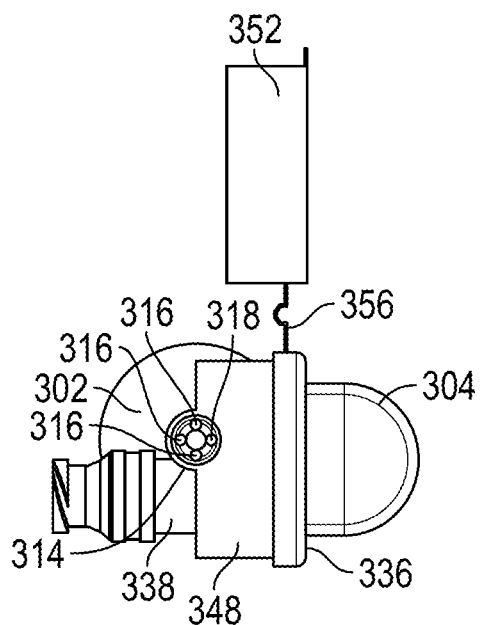
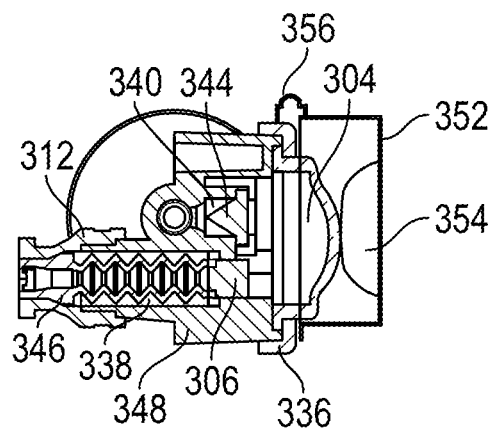
FIG. 7A  FIG. 7B
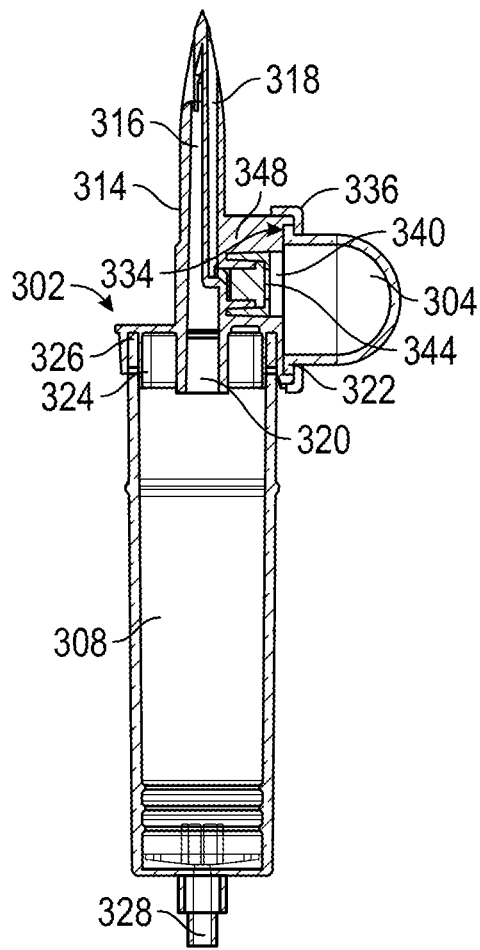
FIG. 8

PRIMING APPARATUS AND METHOD

CROSS-REFERENCE TO RELATED APPLICATION

This is a divisional of U.S. patent application Ser. No. 14/712,634, filed on May 14, 2015, entitled "PRIMING APPARATUS AND METHOD," the disclosure of which is hereby incorporated by reference in its entirety for all purposes.

BACKGROUND

The present disclosure relates generally to a fluid delivery priming system. More particular, it relates to a priming device to remove air from within tubing coupled to a medical fluid reservoir.

Fluid delivery systems are widely used to transmit and deliver medical fluids, such as medical treatments and blood, to patients. When the fluid is delivered intravenously, it is important to release air from the fluid delivery system to prevent introduction of air into a patient's blood stream. Often, a medical practitioner releases air trapped in the fluid delivery system by directing a liquid in the medical fluid reservoir through tubing until the trapped air is released. After the air is released, the liquid in the tubing begins to be released until the fluid flow path is closed.

SUMMARY

The procedure of flushing trapped air in a fluid delivery system is often conducted over a receptacle, and in some instances (e.g., with chemotherapy treatment), repeated contact with the medical fluid may become harmful to the medical practitioner. In many applications, it is desirable to retain the liquid and gasses of the medical fluid bled from the system, thereby preventing exposure to the medical practitioner.

An aspect of the present disclosure provides a priming system comprising: a resilient chamber having flexible walls; and a first check valve in a first fluid pathway between the resilient chamber and a fluid reservoir, wherein a fluid flows through the first check valve only in a direction from the fluid reservoir toward the resilient chamber; wherein the fluid returns to the fluid reservoir through a second fluid pathway between the resilient chamber and the fluid reservoir upon compression of the walls of the resilient chamber.

According to certain implementations of the present disclosure, the first fluid pathway and the second fluid pathway extend through a housing fluidly coupled to the fluid reservoir. In some instances, the housing comprises a drip chamber between the fluid reservoir and first check valve, wherein the first fluid pathway extends through the drip chamber. In certain implementations, the second fluid pathway extends through the drip chamber.

In certain instances of the present disclosure, the resilient chamber walls expand when the fluid is driven from the fluid reservoir, through the first check valve, and into the resilient chamber. In some implementations, the resilient chamber walls contract and direct the fluid therein through the second fluid pathway and into the fluid reservoir.

In some embodiments of the present disclosure, a second check valve is disposed in the second fluid pathway between the resilient chamber and the fluid reservoir, wherein a fluid flows through the second check valve only in a direction from the resilient chamber to the fluid reservoir. In some implementations, the resilient chamber is hemispherically shaped. Some embodiments provide a hingedly coupled retaining member, wherein in a closed position, the retaining member engages the resilient chamber, such that the resilient chamber walls are impeded from expanding. In some instances, the resilient chamber is an elongated cylinder.

An aspect of the present disclosure provides a priming device comprising: a housing having a first fluid pathway and a second fluid pathway; a resilient chamber having flexible walls, wherein the first fluid pathway and the second fluid pathway are fluidly coupled to the resilient chamber; a first check valve in the first fluid pathway such that a fluid flow through the first check valve is only in a direction toward the resilient chamber; wherein compression of the resilient chamber walls directs a fluid out of the resilient chamber and through the second fluid pathway. According to certain implementations of the present disclosure, the housing comprises a drip chamber such that a fluid received into the first fluid pathway is driven through the drip chamber and the first check valve before entering into the resilient chamber.

In certain instances of the present disclosure, the resilient chamber walls are expanded by the fluid driven into the resilient chamber. In some instances, when not manually depressed, the resilient chamber walls are configured to expand, and expansion of the resilient chamber walls draws a fluid received through the first fluid pathway into the resilient chamber. In some implementations, the resilient chamber is hemispherically shaped. Some embodiments provide a retaining ring is coupled to the housing such that the resilient chamber extends through and is retained by the retaining ring.

In some embodiments of the present disclosure, a second check valve is disposed in the second fluid pathway such that a fluid flow through the second check valve is only in a direction away from the resilient chamber. In certain embodiments, the first fluid pathway and the second fluid pathway each comprises an opening through the housing, each opening being juxtaposed through a portion of the housing, and thereby forming defining a spike. In some embodiments, the first fluid pathway comprises an inlet port. In some instances, the port comprises a flexible valve, wherein in a sealed position the valve seals the inlet port, and in an open position, the valve does not seal the inlet port.

An aspect of the present disclosure provides a method of priming, comprising the steps of: receiving a fluid into a first fluid pathway of a housing; directing the fluid through a first check valve in the first fluid pathway and into a resilient chamber having flexible walls; manually compressing the flexible walls and directing the fluid through a second fluid pathway.

According to certain implementations of the present disclosure, directing the fluid into the resilient chamber causes the flexible walls to expand. Some embodiments provide the step of directing the fluid through a second check valve in the second fluid pathway. Certain embodiments provide the step of receiving the fluid into the first fluid pathway from a fluid reservoir. Some instances provide the step of directing the fluid from the second fluid pathway to the fluid reservoir. Some embodiments provide the step of directing the fluid through a drip chamber coupled to the first fluid pathway between the fluid reservoir and the first check valve.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 7A illustrates a top view of the priming device of FIG. 5.

FIG. 7B illustrates a top sectional view of the priming device of FIG. 5.

FIG. 8 illustrates a front sectional view of the priming device of FIG. 5.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1A:
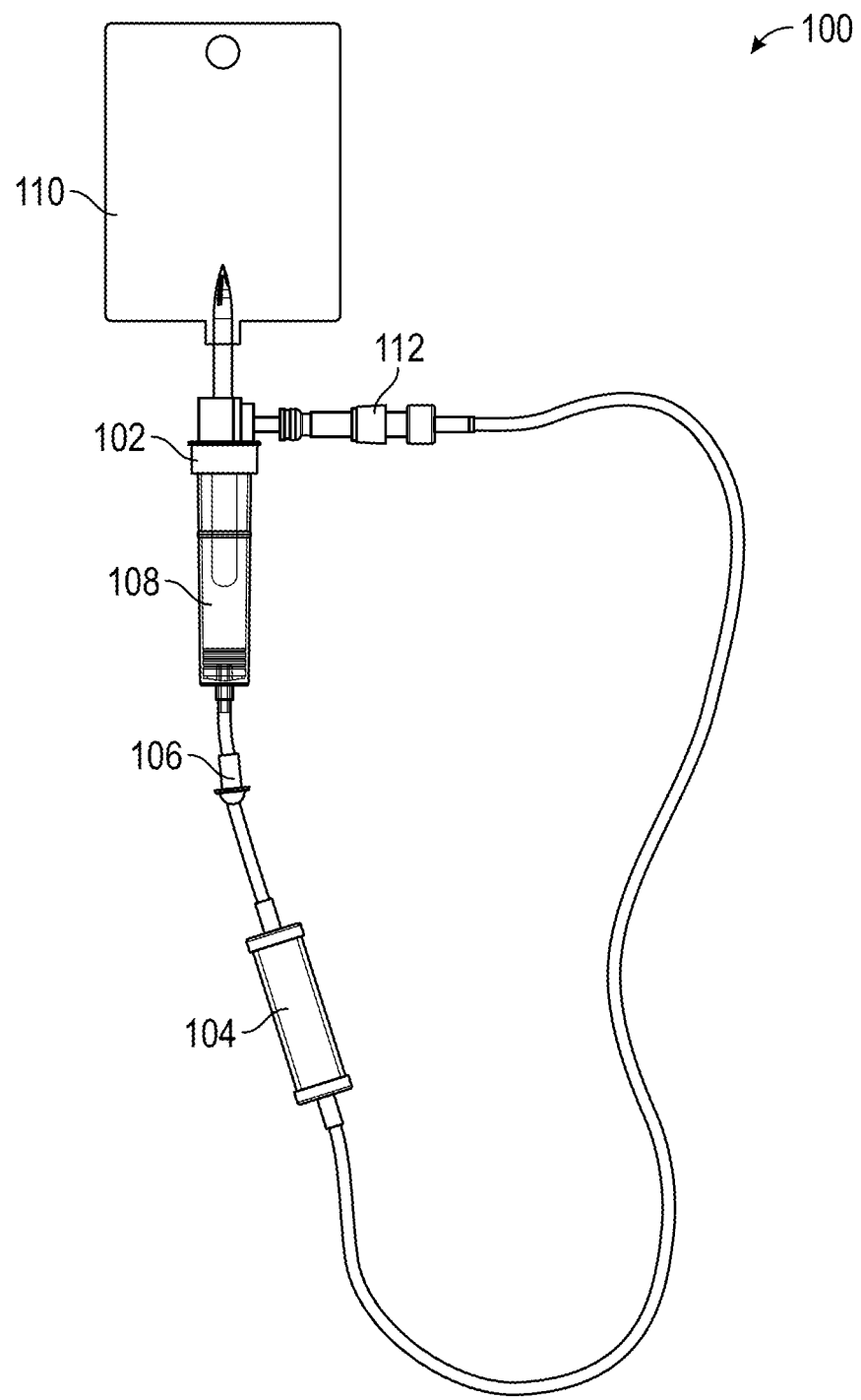
FIG. 1A illustrates an embodiment of a priming system in accordance with aspects of the present disclosure.
Figure 1B:
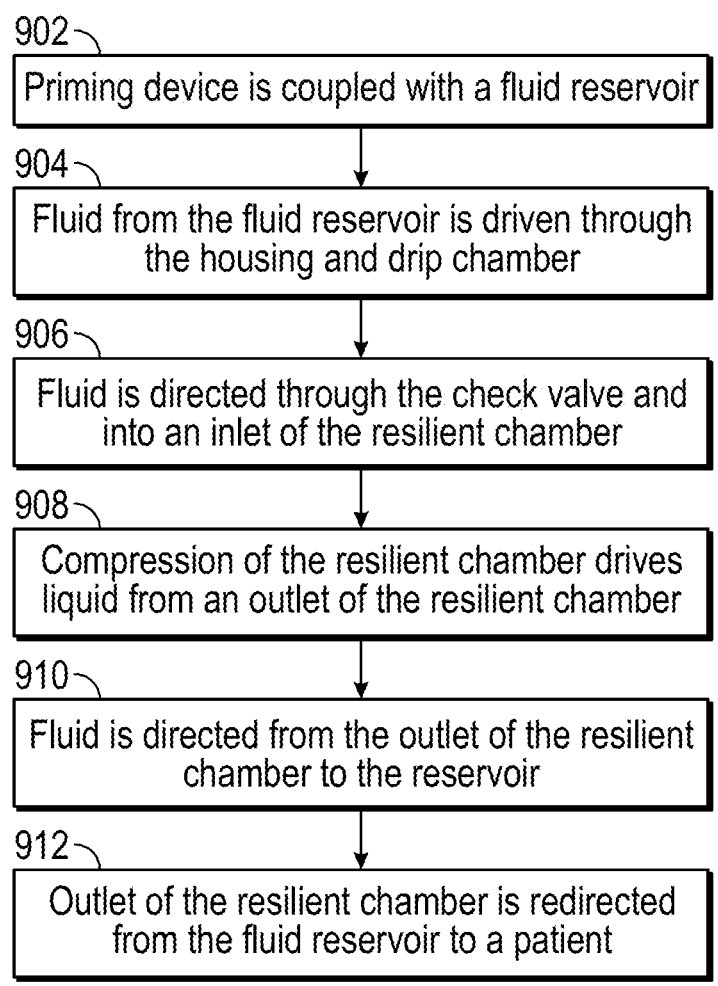
FIG. 1B is a flowchart illustrating operation of a priming system in accordance with aspects of the present disclosure.
Figure 2:
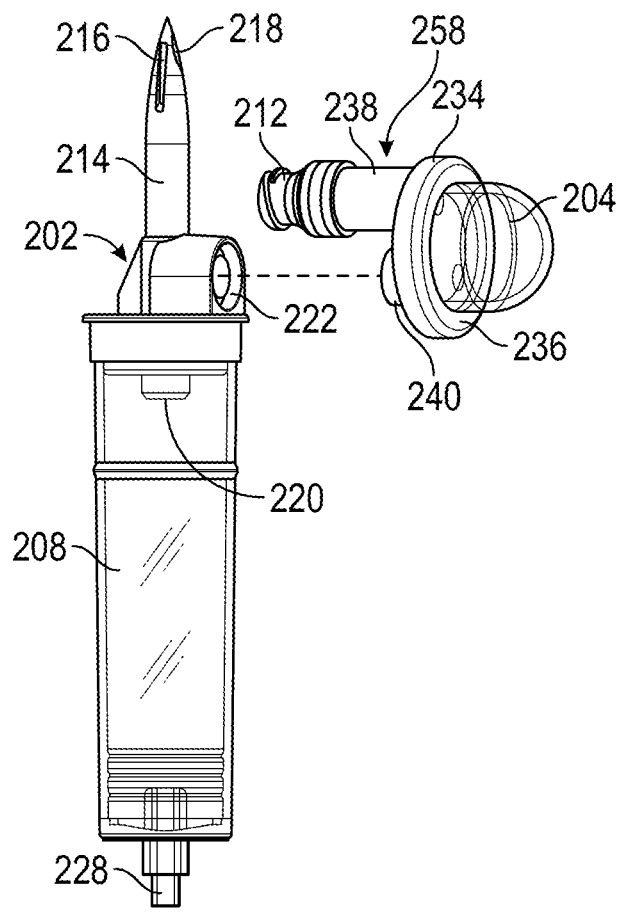
FIG. 2 illustrates a front view of an embodiment of a priming device in accordance with aspects of the present disclosure.
Figure 3:
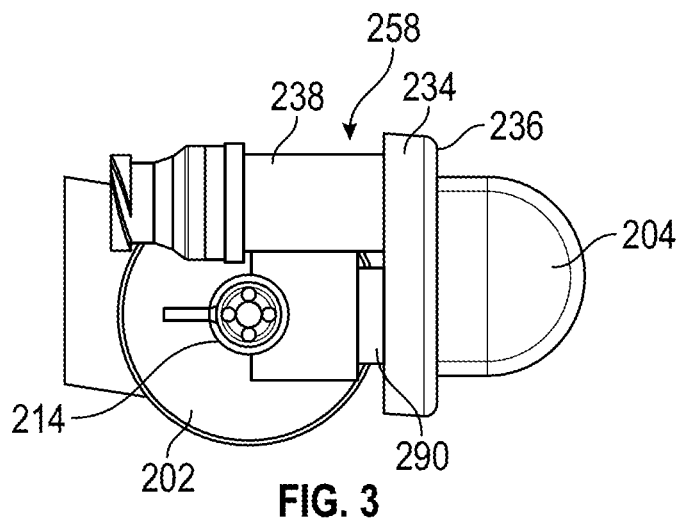
FIG. 3 illustrates a top view of the priming device of FIG. 2.

FIG. 1A illustrates an embodiment of a priming system 100 having a housing 102, a resilient chamber 104, a check valve 106, a drip chamber 108, and a fluid reservoir 110. Referring to FIG. 1B, a flowchart illustrates operation of a priming system in accordance with aspects of the present disclosure. A priming device housing is fluidly coupled with the fluid reservoir in step 902. Fluid is driven from the fluid reservoir, through the housing and a drip chamber in step 904. From the drip chamber, the fluid is directed through a check valve and into an inlet of a resilient chamber in step 906. Compression of the resilient chamber causes the fluid, which comprises a liquid and a gas, to be driven from an outlet of the resilient chamber in step 908. The liquid and gas are then directed from the resilient chamber back to the fluid reservoir in step 910. During this operation, liquid from the fluid reservoir is drawn through the priming system, thereby causing the gas to be collected within the fluid reservoir. This operation is repeated until gases trapped within the priming system, or more specifically within tubing of the priming system, are reduced to a satisfactory level or until the gasses are sufficiently collected within or conducted to the fluid reservoir. In some instances, the gasses are sufficiently collected within or conducted to the fluid reservoir when there are substantially no visible air bubbles or pockets contained in tubing of the priming system. Once the gas is reduced to a satisfactory level, the outlet of the resilient chamber can be redirected from the fluid reservoir to a patient or a pump in step 912. In some embodiments, the outlet of the resilient chamber is removably coupled with the fluid reservoir through a needleless medical connector.

Referring to FIGS. 2-4B, embodiments of a priming device are illustrated having a resilient chamber 204 and a check valve 206. The priming device includes a housing 202, which can include a spike portion 214 configured to be inserted into a port of a fluid reservoir. A tip of the spike portion 214, distal from the housing, includes an inlet passage 216 and an outlet passage 218. The housing further includes an opening 220 fluidly coupled with the inlet passage 216. The housing also includes a housing port 222 fluidly coupled with the outlet passage 218.

When the spike portion 214 is inserted into a port of a fluid reservoir, the inlet passage 216 permits conduction of a fluid from within the fluid reservoir to enter the housing 202 or to travel from the housing 202 into the fluid reservoir. The outlet passage 218 also permits fluid conduction between the housing 202 and the fluid reservoir. In some embodiments, the inlet passage 216 primarily functions to conduct a fluid from within the fluid reservoir to the housing 202, and the outlet passage 218 functions to conduct fluid from the housing 202 to the fluid reservoir.

A portion of the housing 202, opposite the tip of the spike portion 214, forms a circumferential ridge 224 around the opening 220. A drip chamber 208 forming, for example, an elongated cylinder is coupled to the opening 220 of the housing 202. An open first end 226 of the drip chamber 208 is inserted over the circumferential ridge 224 such that the opening 220 is fluidly coupled with the drip chamber 208.

Figures 4A, 4B:
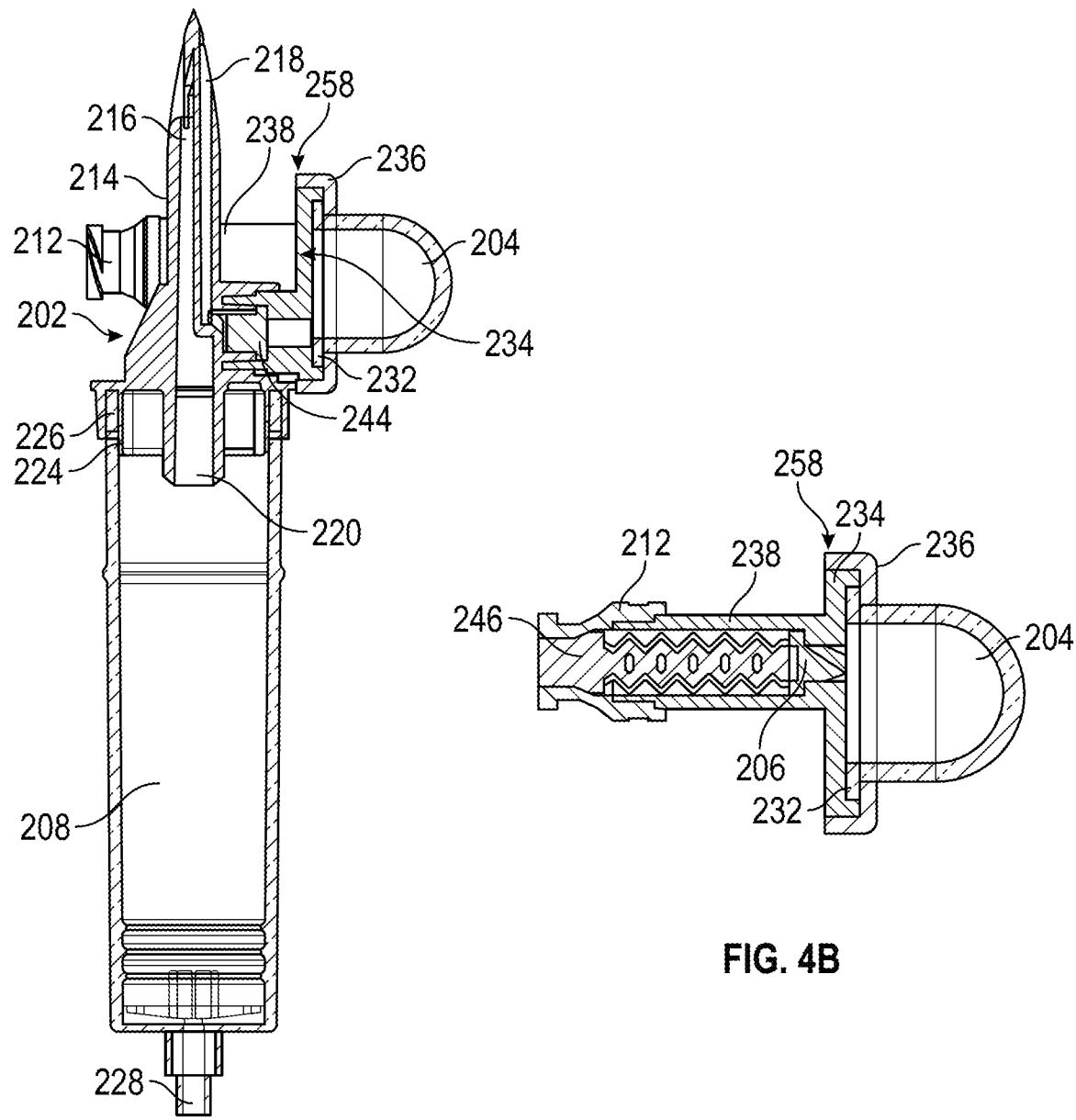
FIG. 4A illustrates a front sectional view of the priming device of FIG. 2.
FIG. 4B illustrates a front sectional view of a portion of the priming device of FIG. 2.

Referring to FIGS. 4A-4B, a resilient chamber 204 is fluidly coupled to the housing port 222 through a manifold 258 such that the check valve 206 is between the fluid reservoir and the resilient chamber 204. The check valve 206 limits a fluid flow only a direction from the fluid reservoir toward the resilient chamber 204, and prevents a fluid from flowing toward the fluid reservoir through the inlet passage 216 when pressure within the resilient chamber 204 is increased (e.g., when the resilient chamber 204 is compressed).

The resilient chamber 204 is shaped as a cylinder having a domed portion and an opening opposite the domed portion. A flange 232 surrounds the opening and extends radially outward from the resilient chamber 204. The resilient chamber 204 comprises a resilient material such that the cylinder walls and domed portion return to a neutral shape after being expanded or compressed. The material and shape are selected such that after being deformed by compression, the resilient chamber 204 has sufficient expansive force to draw in fluid from the fluid reservoir. In some embodiments, the resilient chamber 204 is composed of a material such as nylon, polyurethane, polyethylene terephthalate (PET), or polyvinyl chloride. However, the resilient chamber 204 can be other elastomers. In some embodiments, the thickness of the resilient chamber 204 is from 0.015" to 0.100" and has a Shore hardness from A 20 to 80.

The opening of the resilient chamber 204 is coupled to a portion of the manifold 258 forming a seat 234. The seat 234 includes a circumferential planar surface configured to receive and enclose the opening of the resilient chamber 204. In some embodiments, a plane formed by the surface of the flange 232 is received within a ridge formed around the perimeter of the seat 234. The resilient chamber 204 is retained against the seat 234 by a circumferential retaining ring 236 which extends around the resilient chamber 204 and couples with the ridge portion of the seat 234. When the retaining ring 236 is coupled to the seat 234, the flange 232 of the resilient chamber 204 is captured between the retaining ring 236 and seat 234 to form a fluid-tight seal between the resilient chamber 204 and the manifold 258.

The manifold 258 comprises an inlet port 238 and an outlet port 240. In some embodiments, the inlet port 238 and the outlet port 240 form fluid passages that extend coaxially with the manifold 258 and seat 234 and through the seat 234. A check valve 206 (e.g., a first check valve) is retained within the inlet port 238, thereby limiting a fluid flow only a direction through the manifold 258 toward the resilient chamber 204. When the resilient chamber 204 is compressed, pressure within the chamber is increased. The increased pressure drives the fluid out of the resilient chamber 204. Due to the check valve 206 in the inlet port 238, the fluid is directed from the resilient chamber 204 through the outlet port 240.

In some embodiments, the inlet port 238 includes a needleless medical connector 212. The needleless medical connector 212 includes a valve 246 disposed within the inlet port 236. In a sealed position the valve 246 seals the inlet port 238, and in an open position, the valve 246 does not seal the inlet port 238.

The outlet port 240 of the manifold 258 is fluidly coupled with the housing port 222. In some embodiments, the outlet port 240 includes a check valve 244 (e.g., a second check valve), thereby limiting a fluid flow only a direction through the manifold 258 from the resilient chamber 204 toward the housing port 222. In some embodiments the check valve 244 is retained in the coupling between the outlet port 240 and the housing port 222, or in the outlet passage 218 of the housing 202. In some embodiments, the check valves 206 and 244 are a duckbilled check valve. However, the check valves 206 and 244 may be any type of valve that normally allows fluid to flow through the valve in only one direction, such as an umbrella valve or disk valve.

In operation, the spike portion 214 is inserted into a port of a fluid reservoir (FIG. 1A) such that the inlet passage 216 and the outlet passage 218 are in fluid communication with the fluid reservoir. Fluid from the fluid reservoir begins to enter the housing 202 through the inlet passage 216. The fluid, which may contain both liquid and gas, passes through the opening 220 of the housing 202 and begins to fill the drip chamber 208 and a segment of tubing (not shown) coupled to an opening at a second end 228 of the drip chamber 208. To prepare the system for patient use, the tubing should be substantially free of gas by flushing the tubing with liquid from the fluid reservoir until the gas is substantially removed from the tubing and the tubing of the system is filled with liquid. This process is called priming the fluid delivery system.

The fluid delivery system is primed by coupling a second end of the tubing to the inlet port 238 of the manifold 258. To begin priming, the resilient chamber 204 must be at least partially filled with the fluid. In some embodiments, the fluid is driven into the resilient chamber 204 by compressing the fluid reservoir or the drip chamber 208. In an embodiment, fluid is drawn into the resilient chamber 204 by compressing and releasing the resilient chamber 204. As the compressed resilient chamber 204 returns to its neutral shape, fluid is drawn from the fluid reservoir into the resilient chamber 204. In either instance, the fluid passes through the check valve 206 of the inlet port 238 as it enters the resilient chamber 204. Next, the resilient chamber 204 is compressed, thereby driving the liquid and gas through the outlet port 240 of the resilient chamber 204. The liquid and gas are prevented, or impeded, from exiting the resilient chamber 204 through the inlet port 238 by the check valve 206. The liquid and gas exiting the resilient chamber 204 through the outlet port 240 are then directed through the outlet passage 218 of the housing 202 and into the fluid reservoir.

As the resilient chamber 204 is repeatedly compressed and released, liquid from the fluid reservoir is drawn into the priming system and fluid, containing liquid and gas, is returned into the fluid reservoir. Once gas is no longer present in the fluid delivery system, or reduced to a satisfactory level (e.g., such that there are substantially no visible bubbles or pockets of gas throughout the tubing of the system), the second end of the tubing may be disconnected from the inlet port 238 and redirected to a catheter, pump, or other delivery device for delivery of the fluid to the patient.

Referring to FIGS. 5-8, an embodiment of a priming device is illustrated having a resilient chamber 304 and a check valve 306. The priming device includes a housing 302 having a spike portion 314 configured to be inserted into a port of a fluid reservoir. A tip of the spike portion 314, distal from the housing, includes an inlet passage 316 and an outlet passage 318. The housing further includes an opening 320 fluidly coupled with the inlet 316.

Similar to that described above with respect to certain embodiments depicted in FIGS. 2-4B, except as expressly contradicted below, when the spike portion 314 is inserted into a port of a fluid reservoir, the inlet passage 316 permits conduction of a fluid from within the fluid reservoir to enter the housing 302 or to travel from the housing 302 into the reservoir. The outlet passage 318 also permits fluid conduction between the housing 302 and the fluid reservoir.

A portion of the housing 302, opposite the tip of the spike portion 314, forms a circumferential ridge 324 around the opening 320. A drip chamber 308 forming an elongated cylinder is coupled to the opening 320 of the housing 302. An open first end 326 of the drip chamber 308 is inserted over the circumferential ridge 324 such that the opening 320 is fluidly coupled with the drip chamber 208.

In some embodiment, a portion of the housing extends radially outward from an axis defined by the spike portion 314 to form a base 348. An end of the base 348, distal from the housing 302, comprises a planar surface forming a seat 334. The base 348 includes an inlet port 338 and an outlet port 340 forming fluid passages that extend through and coaxially with the seat 334 of the base 348.

Figure 6:
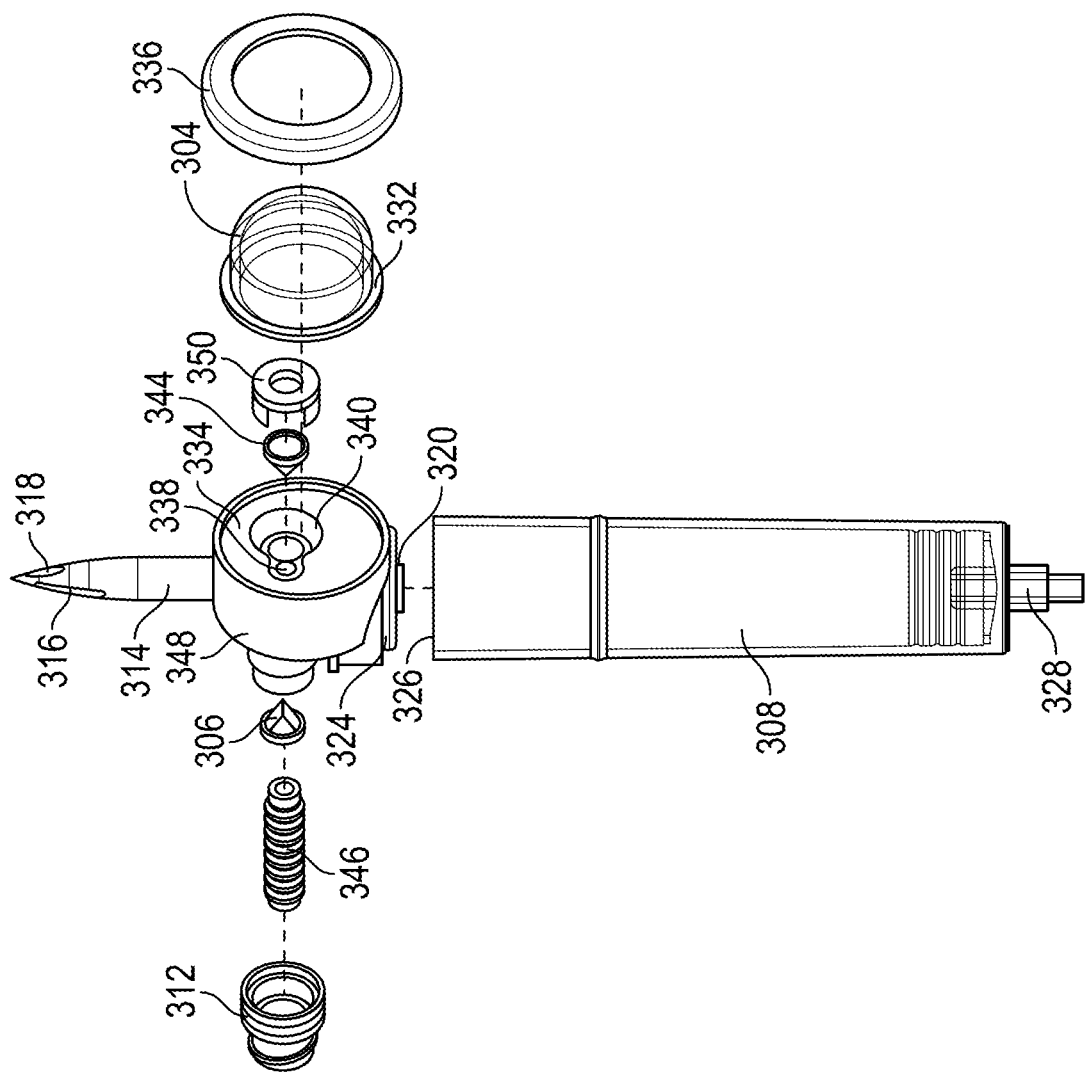
FIG. 6 is an exploded view of the priming device of FIG. 5.
Figure 5:
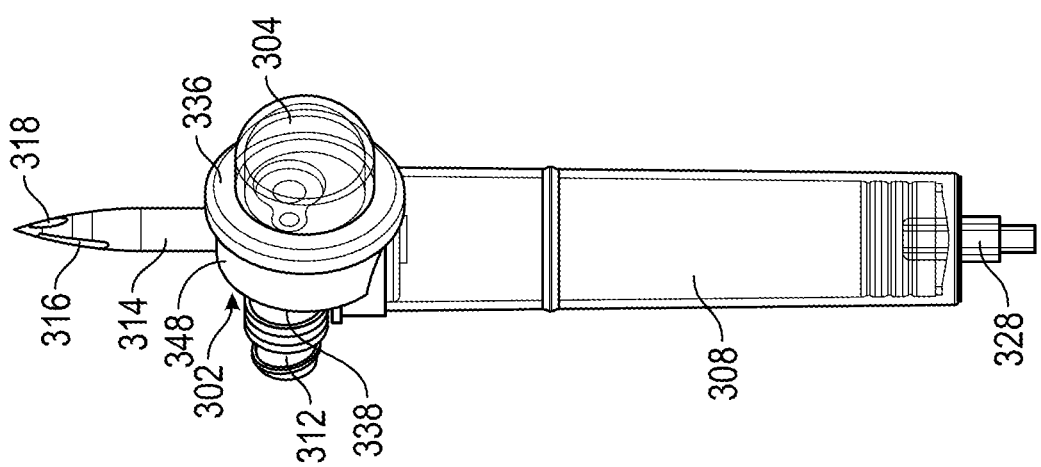
FIG. 5 illustrates a front view of an embodiment of a priming device in accordance with aspects of the present disclosure.

Referring to FIGS. 6-8, a resilient chamber 304 is coupled to the seat 334 of the housing 302 such that the check valve 306 is between the fluid reservoir and the resilient chamber 304. The check valve 306 limits a fluid flow only a direction from the fluid reservoir toward the resilient chamber 304, and prevents a fluid from flowing toward the fluid reservoir through the inlet passage 316 when pressure within the resilient chamber 304 is increased (e.g., when the resilient chamber 304 is compressed).

The resilient chamber 304 is shaped as a cylinder having a domed portion and an opening opposite the domed portion. A flange 332 surrounds the opening and extends radially outward from the resilient chamber 304. The resilient chamber 304 comprises a resilient material such that the cylinder walls and domed portion will return to neutral shape after being expanded or compressed. The material and shape are selected such that after being deformed by compression, the resilient chamber 304 has sufficient expansive force to draw in fluid from the fluid reservoir. In some embodiments, the material is the same as, or is structurally and/or functionally equivalent to that described above in connection with FIGS. 2-4B.

When the opening of the resilient chamber 304 is placed against the seat 334, the opening of the resilient chamber 304 is received and enclosed by the seat 334. A plane formed by the surface of the flange 332 is received within a ridge formed around the perimeter of the seat 334. The resilient chamber 304 is retained against the seat 334 by a circumferential retaining ring 336 which extends around the resilient chamber 304 and couples with the ridge portion of the seat 334. When the retaining ring 336 is coupled to the seat 334, the flange 332 is captured between the retaining ring 336 and seat 334 to form a fluid-tight seal.

The inlet port 338 extends through the base 348 and the seat 334. The check valve 306 is retained within the inlet port 338, thereby limiting a fluid flow only a direction toward the resilient chamber 304.

When the resilient chamber 304 is compressed, pressure within the chamber is increased. The increased pressure drives the fluid out of the chamber. Due to the check valve 306 in the inlet port 338, the fluid is directed from the resilient chamber 204 through the outlet port 340.

In some embodiments, the inlet port 338 includes a needleless medical connector 312. The needleless medical connector 312 includes a valve 346 disposed within the inlet port 336. In a sealed position the valve 346 seals the inlet port 338, and in an open position, the valve 346 does not seal the inlet port 338.

Referring to FIGS. 7B and 8, the outlet port 340 is fluidly coupled with the outlet passage 318 of the spike portion 314. Referring to FIG. 6, the outlet port 340 is shaped as a well extending through the planar surface of the seat 334, partially toward into the base 348 in a direction toward the spike portion 314 of the housing 302. In some embodiments, the outlet port 340 includes a check valve 344 to limit a fluid flow through the check valve 344 only a direction away from the resilient chamber 304. In some embodiments, the check valve 306 is a duckbilled check valve. However, the check valve 306 may be any type of valve that normally allows fluid to flow through the valve in only one direction, such as an umbrella valve or disk valve.

In some embodiments the check valve 344 is seated in a cradle 350 having a fluid passage therethrough. In an embodiment, the cradle 350 is shaped as a cylinder having an open first end with notches through the cylinder wall, and an open second end with a circumferential ridge extending partially inward from the circumference of the cylinder. The open first end of the cradle 350 is then inserted into the outlet port 340 with the check valve 344 therein such that a fluid may flow through the open second end of the cradle 350 and check valve 344. In some embodiments, the cradle 350 is press fit into the outlet port 344 from the planar surface of the seat 334. In some embodiments, the cradle 350 is coupled to the outlet port 344 using a bonding material or other ultrasonic welding.

Referring to FIGS. 7A and 7B, a retaining member 352 is illustrated in an open position and closed position, respectively. In some embodiments, the retaining member 352 is cylindrical having an open first end, a closed second end, and an inner cavity. The open first end of the retaining member 352 comprises an inner cross-sectional width that is larger than the cross-section of the resilient chamber 304. A protrusion 354 extends into the inner cavity from the inner surface of the closed second end. In the closed position, the open first end of the retaining member 352 is affixed to the housing 302 such that the resilient chamber 304 extends into the inner cavity. In the closed position, the protrusion 354 engages the resilient chamber 304 such that the walls and domed portion are impeded from expanding. In some embodiments, the protrusion 354 is a dome inversely oriented to the dome of the resilient chamber 304 when the retaining member 352 is in a closed position. In some embodiments, the distance between the open first end and closed second end of the retaining member 352 is less than a length of the resilient chamber 304, such that in the closed position the inner surface engages the resilient chamber 304. The retaining member 352 is preferably coupled to the housing 302 by a hinge 356. In some embodiments, retaining member 352 is rotatably coupled to the retaining ring 336 by a living hinge 356. In some embodiments, the open first end of the retaining member 352, and the retaining ring 336, comprise mating threads such that the retaining member 352 can be threadably attached to the retaining ring 336.

In operation, the spike portion 314 is inserted into a port of a fluid reservoir (not shown) such that the inlet passage 316 and the outlet passage 318 are in fluid communication with the fluid reservoir. Fluid from the fluid reservoir begins to enter the housing 302 through the inlet passage 316. The fluid, which may contain both liquid and gas, passes through the opening 320 of the housing 302 and begins to fill the drip chamber 308 and a segment of tubing (not shown) coupled to an opening at a second end 328 of the drip chamber 308. To remove the gas, the fluid delivery system must be primed.

The fluid delivery system is primed by coupling a second end of the tubing to the inlet port 338 of the seat 334. To begin priming, the resilient chamber 304 must be at least partially filled with the fluid. In some embodiments, the fluid is driven into the resilient chamber 304 by compressing the fluid reservoir or the drip chamber 308. In some embodiments, fluid is drawn into the resilient chamber 304 by compressing and releasing the resilient chamber 304. As the compressed resilient chamber 304 returns to its neutral shape, fluid is drawn from the fluid reservoir into the resilient chamber 304. In either instance, the fluid passes through the check valve 306 of the inlet port 338 as it enters the resilient chamber 304. Next, the resilient chamber 304 is compressed, thereby driving the liquid and gas through the outlet port 340 of the resilient chamber 304. The liquid and gas are prevented, or impeded, from exiting the resilient chamber 304 through the inlet port 338 by the check valve 306. The liquid and gas exiting the resilient chamber 304 through the outlet port 340 are then directed through the outlet passage 318 of the housing 302 and into the fluid reservoir.

As the resilient chamber 304 is repeatedly compressed and released, liquid from the fluid reservoir is drawn into the priming system and fluid, containing liquid and gas, is returned into the fluid reservoir. Once gas is no longer present in the fluid delivery system, or reduced to a satisfactory level, the second end of the tubing may be disconnected from the inlet port 338 and redirected to a catheter, pump, or other delivery device for delivery of the fluid to the patient. Additionally, the retaining member 352 is affixed to the housing 302 such that the resilient chamber 304 remains compressed, and to prevent access to the resilient chamber 304 is prevented. Retaining the resilient chamber 304 in a compressed state reduces the amount of undeliverable fluid remaining within the device after priming.

Figure 9:
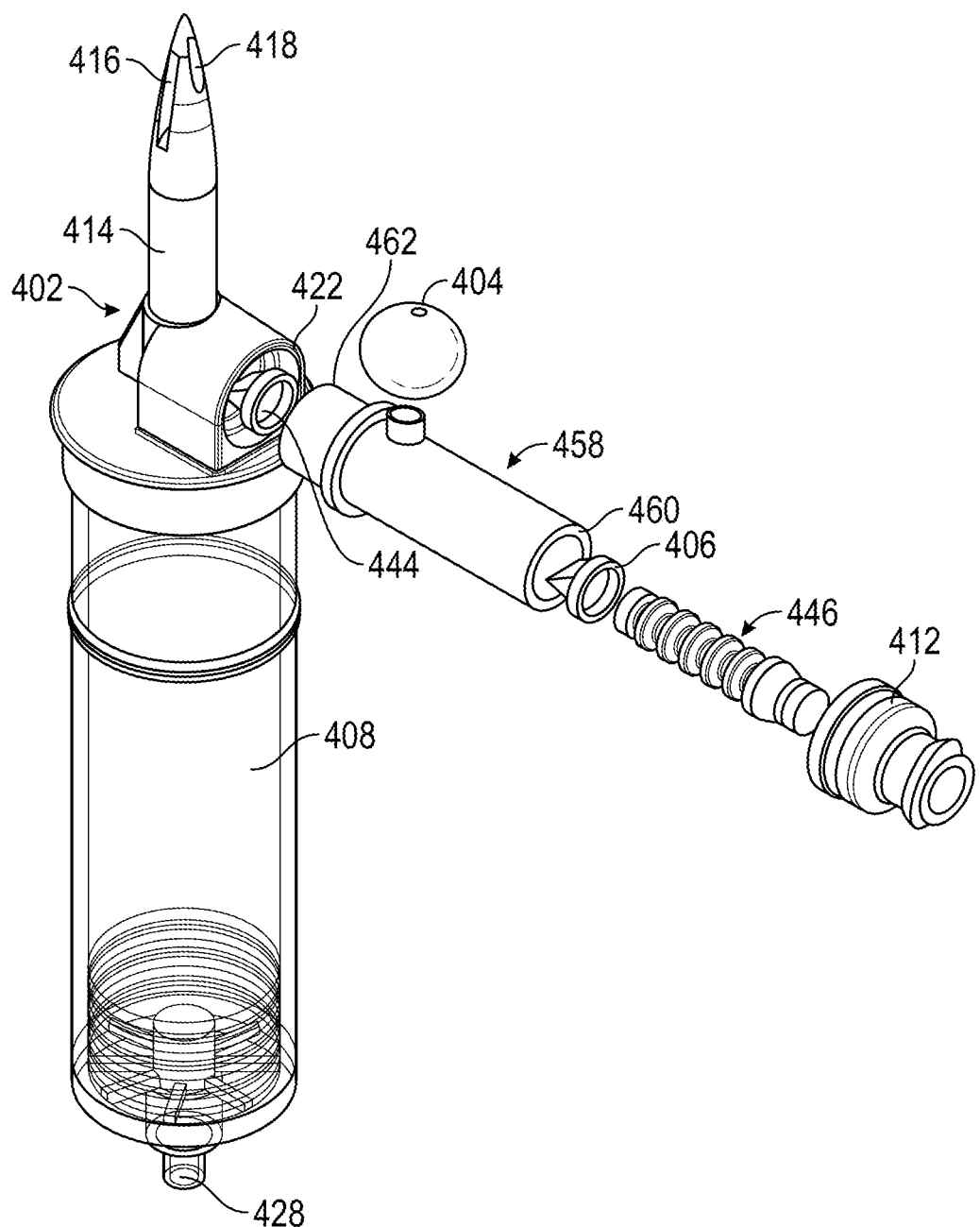
FIG. 9 illustrates a partially exploded front perspective view of an embodiment of a priming device in accordance with aspects of the present disclosure.
Figure 10:
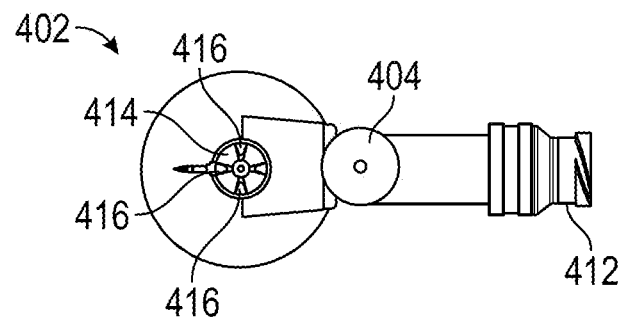
FIG. 10 illustrates a top view of the priming device of FIG. 9.
Figure 11:
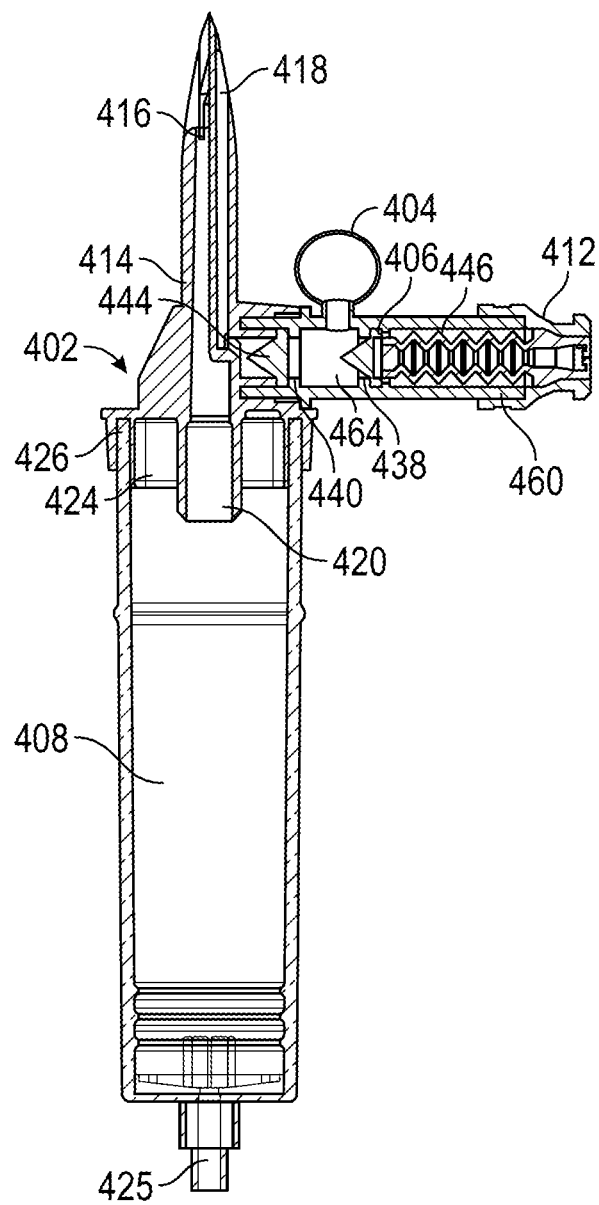
FIG. 11 illustrates a front sectional view of the priming device of FIG. 9.

Referring to FIGS. 9-11, an embodiment of a priming device is illustrated having a resilient chamber 404 and a check valve 406. The priming device includes a housing 402 having a spike portion 414 configured to be inserted into a port of a fluid reservoir. A tip of the spike portion 414, distal from the housing, includes an inlet passage 416 and an outlet passage 418. The housing further includes an opening 420 fluidly coupled with the inlet passage 416 and a housing port 422 fluidly coupled with the outlet 418.

When the spike portion 414 is inserted into a port of a fluid reservoir (not shown), the inlet passage 416 permits conduction of a fluid from within the fluid reservoir to enter the housing 402, and the outlet 418 permits a fluid to return from the housing 402 into the fluid reservoir.

A portion of the housing 402, opposite the tip of the spike portion 414, forms a circumferential ridge 424 around the opening 420. A drip chamber 408 forming an elongated cylinder is coupled to the opening 420 of the housing 402. An open first end 426 of the drip chamber 408 is inserted over the circumferential ridge 424 such that the opening 420 is fluidly coupled with the drip chamber 408.

A resilient chamber 404 is fluidly coupled to the housing port 422 through a manifold 458 such that the check valve 406 is between the fluid reservoir and the resilient chamber 404. The check valve 406 limits a fluid flow only a direction from the fluid reservoir toward the resilient chamber 404, and prevents a fluid from flowing toward the fluid reservoir through the inlet passage 416 when pressure within the resilient chamber 404 is increased (e.g., when the resilient chamber 404 is expanded).

The resilient chamber 404 is a bag or balloon having flexible walls. The resilient chamber 404 comprises a resilient material such that the walls will return to neutral shape after being expanded or compressed. The material and shape are selected such that after expanding, the resilient chamber 404 has sufficient restorative force to drive fluid out of the resilient chamber 404 and into the fluid reservoir. In some embodiments, the resilient chamber 244 is composed of a material such as nylon, polyurethane, polyethylene terephthalate (PET), or polyvinyl chloride. However, the resilient chamber 404 can be other elastomers. In some embodiments the thickness of the resilient chamber 404 is from 0.015" to 0.100" and has a Shore hardness from A 20 to 80.

Referring to FIG. 11, the manifold 458 is cylindrically shaped with an open inlet end and an open outlet end opposing the inlet end. An inlet port 438 is formed by a circumferential ridge along the inner surface of the manifold and offset a distance from the inlet end. An outlet port 440 is formed by a circumferential ridge along the inner surface of the manifold and offset a distance from the outlet end. An intermediate chamber 464 is formed in the manifold 458 between the inlet port 438 and the outlet port 440. The resilient chamber 404 is coupled to a passage extending through a wall of the manifold 458 into the intermediate chamber 464.

The check valve 406 is retained within the manifold 458, between the inlet end 460 and the inlet port 438, thereby limiting a fluid flow only a direction through the manifold 458 from the inlet end 460 toward the intermediate chamber 464. When the resilient chamber 404 is expanded, pressure within the chamber is increased. As the restorative force of the resilient chamber 404 causes the walls to compress, the pressure drives the fluid out of the resilient chamber 404. Due to the check valve 406 in the inlet port 438, the fluid is directed from the resilient chamber 404 through the outlet port 440.

In some embodiments, the inlet end 460 includes a needleless medical connector 412. The needleless medical connector 412 includes a valve 446 disposed within the manifold 458, between the inlet end 460 and inlet port 436. In a sealed position the valve 446 seals the inlet port 438, and in an open position, the valve 446 does not seal the inlet port 438.

In some embodiments, the outlet port 440 includes a check valve 444, thereby limiting a fluid flow only a direction through the manifold 458 from the resilient chamber 404 toward the intermediate chamber 464. In some embodiments, the check valve 444 is retained in the coupling between the outlet port 440 and the housing port 422, or in the outlet passage 418 of the housing 402. In some embodiments, the check valves 406 and 444 are a duckbilled check valve. However, the check valves 406 and 444 may be any type of valve that normally allows fluid to flow through the valve in only one direction, such as an umbrella valve or disk valve.

In operation, the spike portion 414 is inserted into a port of a fluid reservoir (not shown) such that the inlet passage 416 and the outlet passage 418 are in fluid communication with the fluid reservoir. Fluid from the fluid reservoir begins to enter the housing 402 through the inlet passage 416. The fluid, which may contain both liquid and gas, passes through the opening 420 of the housing 402 and begins to fill the drip chamber 408 and a segment of tubing 425 coupled to an opening at a second end 428 of the drip chamber 408. To remove the gas, the fluid delivery system must be primed.

The fluid delivery system is primed by coupling a second end of the tubing to the inlet port 438 of the manifold 458. To begin priming, the resilient chamber 404 must be at least partially filled with the fluid. In some embodiments, the fluid is driven into the resilient chamber 404 by compressing the fluid reservoir or the drip chamber 408. The fluid passes through the check valve 406 of the inlet port 438 as it enters the resilient chamber 404. After fluid ceases to be driven into the resilient chamber 404, for example, by stopping compression of the fluid reservoir or the drip chamber 408, the restorative force of the resilient chamber 404 drives liquid and gas out of the resilient chamber 404 and through the outlet port 440. The liquid and gas are prevented from exiting the manifold 458 through the inlet port 438 by the check valve 406. The liquid and gas exiting the resilient chamber 404 through the outlet port 440 are then directed through the outlet passage 418 of the housing 402 and into the fluid reservoir.

As the resilient chamber 404 is repeatedly expanded and contracted, or as the fluid reservoir is compressed, liquid from the fluid reservoir is drawn or directed into the priming system and fluid containing liquid and gas is returned into the fluid reservoir. Once gas is no longer present in the fluid delivery system, or reduced to a satisfactory level, the second end of the tubing may be disconnected from the inlet port 438 and redirected to a catheter, pump, or other delivery device for delivery of the fluid to the patient. Because the restorative force of the resilient chamber 404 causes it to return to a neutral shape, the amount of undeliverable fluid remaining within the resilient chamber 404 is reduced.

Figure 14:
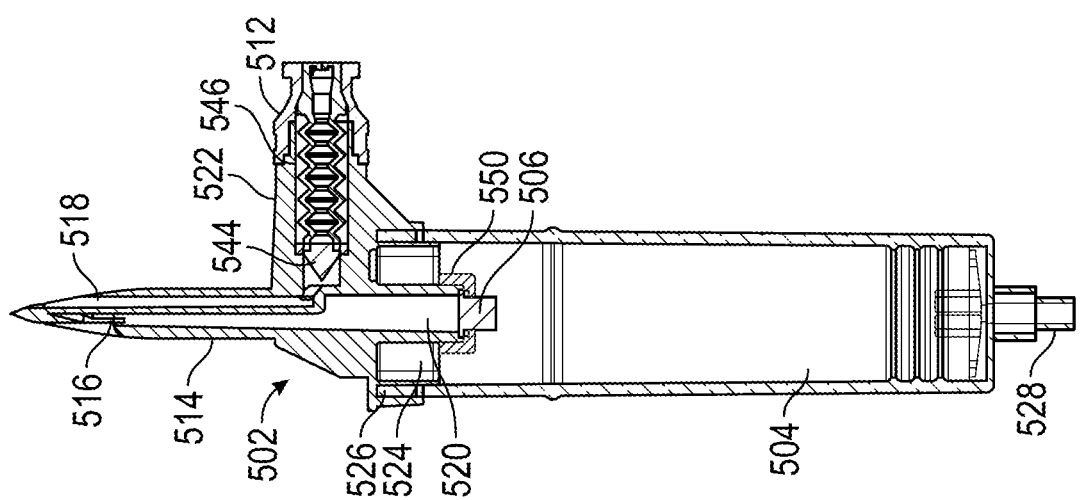
FIG. 14 illustrates a front sectional view of the priming device of FIG. 12.
Figure 13:
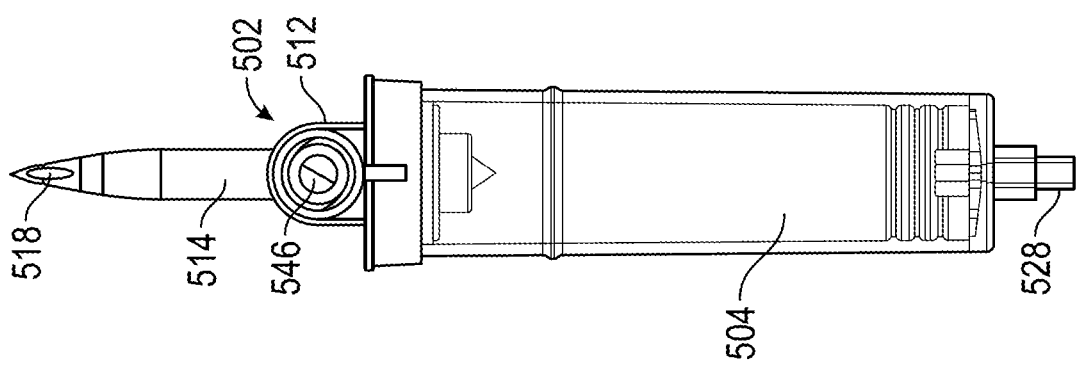
FIG. 13 illustrates a side view of the priming device of FIG. 12.
Figure 12:
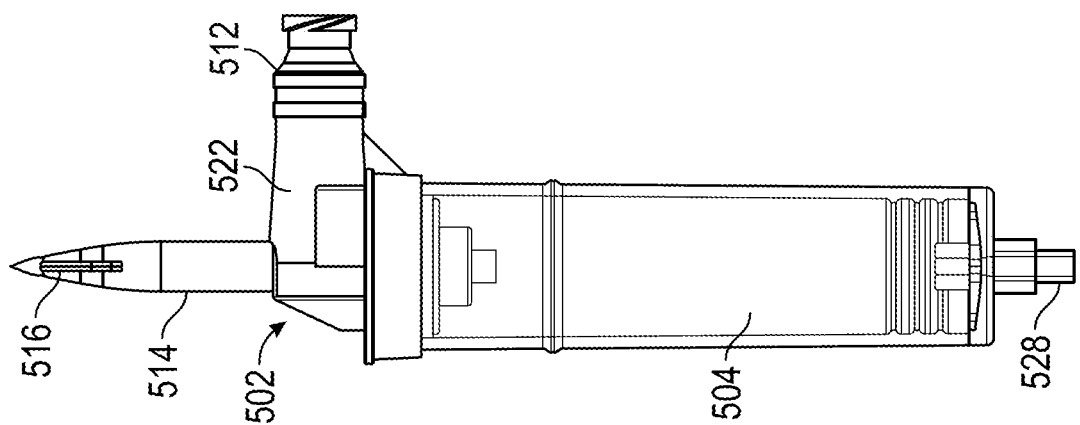
FIG. 12 illustrates a front view of an embodiment of a priming device in accordance with aspects of the present disclosure.

Referring to FIGS. 12-14, an embodiment of a priming device is illustrated having a resilient chamber 504 and a check valve 506. The priming device includes a housing 502 having a spike portion 514 configured to be inserted into a port of a fluid reservoir (not shown). A tip of the spike portion 514, distal from the housing, includes an inlet passage 516 and an outlet passage 518. The housing further includes an opening 520 fluidly coupled with the inlet passage 216 and a housing port 522 fluidly coupled with the outlet passage 518.

When the spike portion 514 is inserted into a port of a fluid reservoir, the inlet passage 516 permits conduction of a fluid from within the fluid reservoir to enter the housing 502, and the outlet 518 permits a fluid to return from the housing 502 into the fluid reservoir.

The check valve 506 is coupled to the inlet passage 516 between the fluid reservoir and the resilient chamber 504. The check valve 506 limits a fluid flow only a direction from the fluid reservoir toward the resilient chamber 504, and prevents a fluid from flowing toward the fluid reservoir through the inlet passage 516 when pressure within the resilient chamber 504 is increased (e.g., when the resilient chamber 504 is compressed).

A portion of the housing 502, opposite the tip of the spike portion 514, forms a circumferential ridge 524 around the opening 520. A resilient chamber 504 (e.g., a drip chamber or priming bulb) forming an elongated cylinder is affixed to the circumferential ridge 524 and fluidly coupled with the opening 520 of the housing 502. An open first end 526 of the resilient chamber 504 is inserted over the circumferential ridge 524 such that the opening 520 is fluidly coupled with the resilient chamber 504. The resilient chamber 504 comprises a resilient material such that the cylinder walls return to a neutral shape after being expanded or compressed. The material and shape are selected such that after being deformed by compression, the resilient chamber 504 has sufficient expansive force to draw in fluid from the fluid reservoir.

The check valve 506 is retained in the opening 520, thereby limiting a fluid flow only a direction through the housing 502, from the inlet passage 516 toward the resilient chamber 504. In some embodiments the check valve 506 is seated in a cradle 550 having a fluid passage therethrough. In an embodiment, the cradle 550 is shaped as a cylinder having an open first end and an open second end with a circumferential ridge extending partially inward from the circumference of the cylinder. The open first end of the cradle 550 is affixed around the opening 520 such that the check valve 506 is retained between the opening 520 and circumferential ridge of the open second end. In an embodiment, the cradle 550 is press fit onto the opening 520.

The housing port 522 includes a check valve 544, thereby limiting a fluid flow only a direction from the housing port 522 toward the outlet 518. In an embodiment, the check valves 506 and 544 are a duckbilled check valve. However, the check valves 506 and 544 may be any type of valve that normally allows fluid to flow through the valve in only one direction, such as an umbrella valve or disk valve. In some embodiments, the housing port 522 includes a needleless medical connector 512. The needleless medical connector 512 includes a valve 546 disposed between the housing port 522 and check valve 544. In a sealed position the valve 546 seals the housing port 522, and in an open position, the valve 546 does not seal the housing port 522.

In operation, the spike portion 514 is inserted into a port of a fluid reservoir (not shown) such that the inlet passage 516 and the outlet passage 518 are in fluid communication with the fluid reservoir. Fluid from the fluid reservoir begins to enter the housing 502 through the inlet passage 516. The fluid passes through the opening 520 of the housing 502 and begins to fill the resilient chamber 504 coupled to a second end 528 of the resilient chamber 504. The fluid which initially begins to fill the resilient chamber 504 may contain both liquid and gas. To remove the gas, the fluid delivery system must be primed.

The fluid delivery system is primed by coupling the second end 528 of the resilient chamber 504 with the housing port 522 through tubing. To begin priming, the resilient chamber 504 must be at least partially filled with the fluid. In some embodiments, the fluid is driven into the resilient chamber 504 by compressing the fluid reservoir. In some embodiments, fluid is drawn into the resilient chamber 504 by compressing and releasing the resilient chamber 504. As the compressed resilient chamber 504 returns to its neutral shape, fluid is drawn from the fluid reservoir into the resilient chamber 504. In either instance, the fluid passes through the check valve 506 at the opening 520 as it enters the resilient chamber 504. Next, the resilient chamber 504 is compressed, thereby driving the liquid and gas through the second end 528 of the resilient chamber 504. The liquid and gas are prevented, or impeded, from exiting the resilient chamber 504 through the inlet port 538 by the check valve 506. The liquid and gas exiting the resilient chamber 504 through the second end 528 are then directed through tubing to the housing port 522 and into the fluid reservoir.

As the resilient chamber 504 is repeatedly compressed and released, liquid from the fluid reservoir is drawn into the priming system and fluid, containing liquid and gas, is returned into the fluid reservoir. Once gas is no longer present in the fluid delivery system, or reduced to a satisfactory level, the tubing may be disconnected from the housing port 522 and redirected to a catheter, pump, or other delivery device for delivery of the fluid to the patient.

Figure 15:
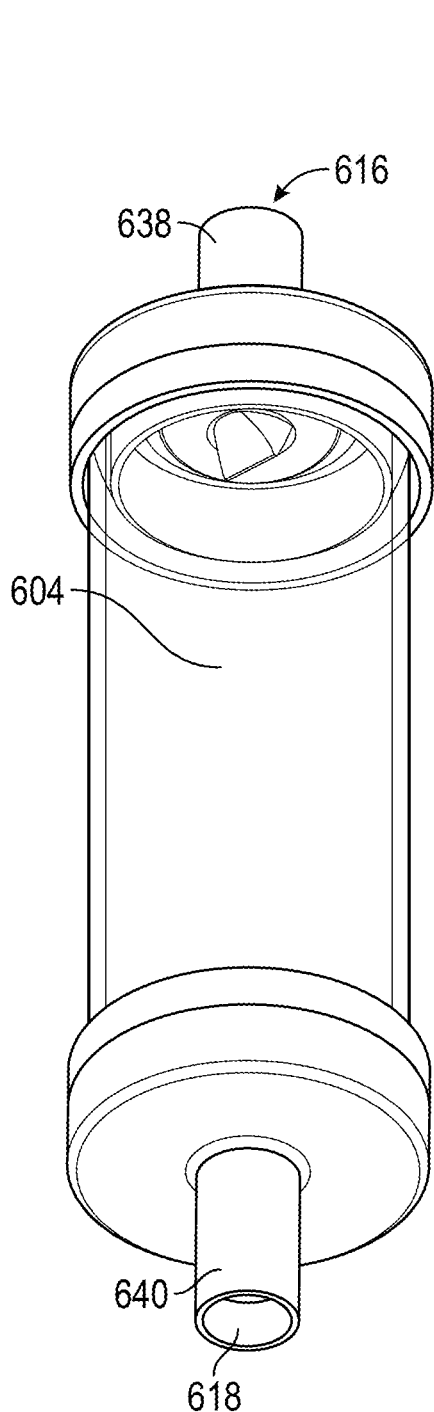
FIG. 15 illustrates a front perspective view of an embodiment of a priming device in accordance with aspects of the present disclosure.
Figure 16:
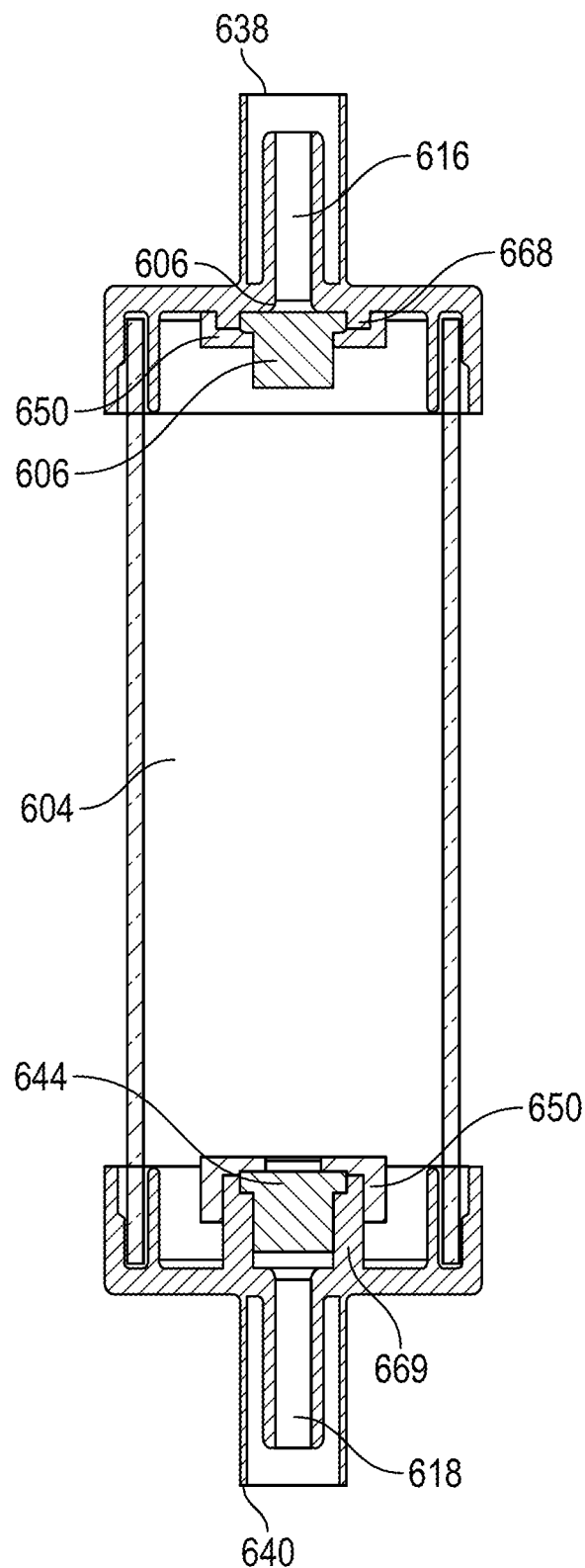
FIG. 16 illustrates a front sectional view of the priming device of FIG. 15.
Figure 17:
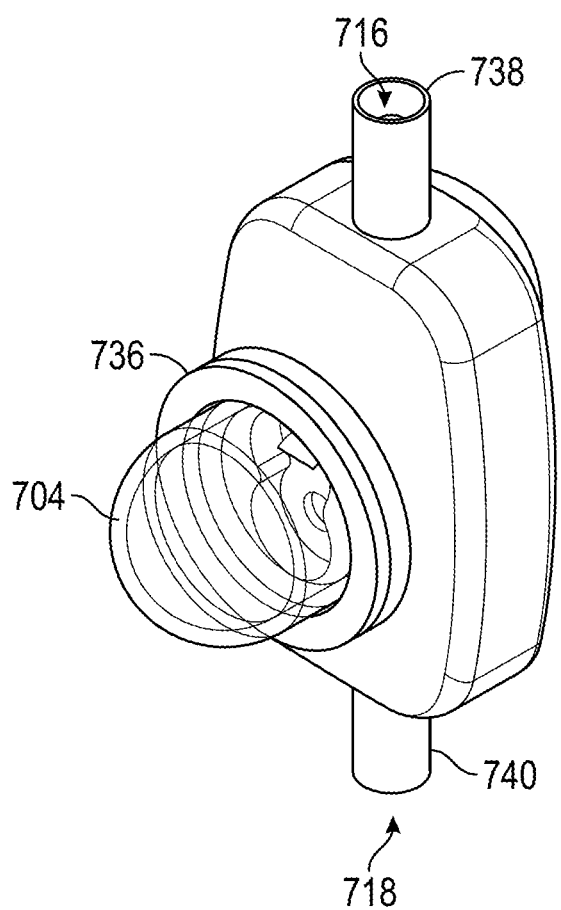
FIG. 17 illustrates a front perspective view of an embodiment of a priming device in accordance with aspects of the present disclosure.
Figure 21:
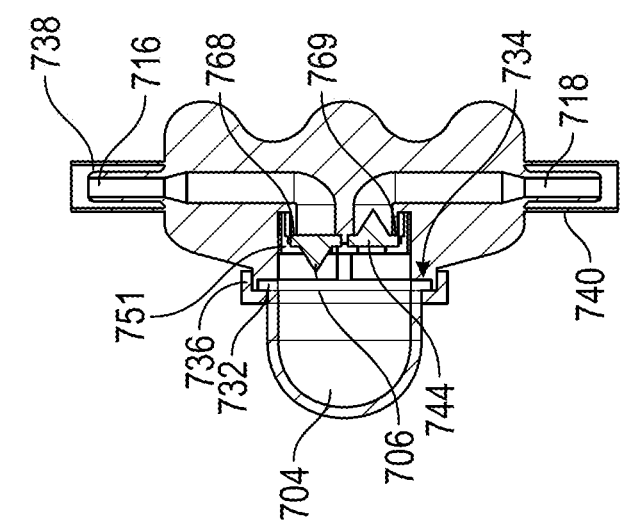
FIG. 21 illustrates a side sectional view of the priming device of FIG. 17.
Figure 18:
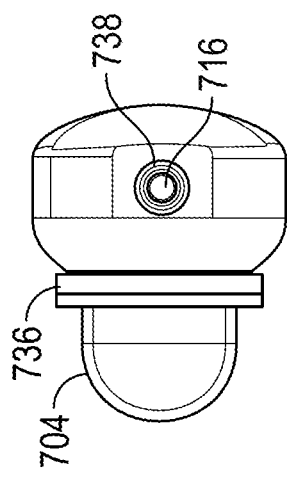
FIG. 18 illustrates a top view of the priming device of FIG. 17.
Figure 20:
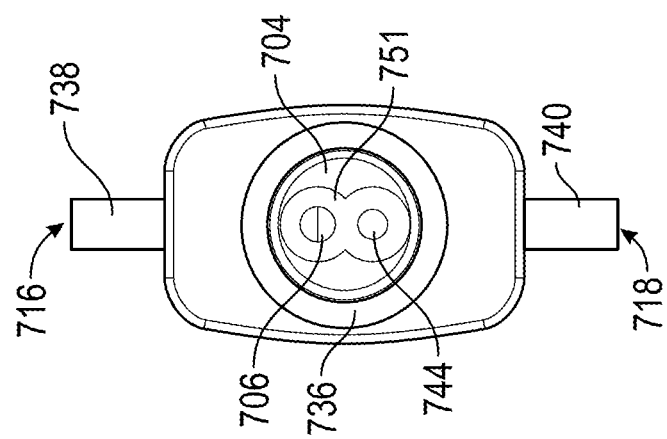
FIG. 20 illustrates a front view of the priming device of FIG. 17.
Figure 19:
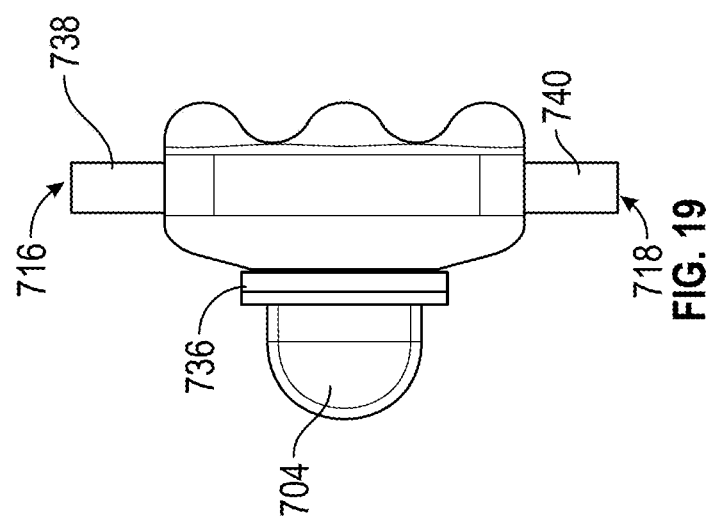
FIG. 19 illustrates a side view of the priming device of FIG. 17.

Referring to FIGS. 15-16, an embodiment of a priming device is illustrated having a resilient chamber 604 and a check valve 606. The priming device includes a cylindrically shaped resilient chamber 604 having an open first end and an open second end. The resilient chamber 604 comprises a resilient material such that the cylinder walls return to a neutral shape after being expanded or compressed. The material and shape are selected such that after being deformed by compression, the resilient chamber 604 has sufficient expansive force to draw in fluid from a fluid reservoir through the first end.

Between the fluid reservoir and the resilient chamber 604, a check valve 606 limits a fluid flow only a direction from the fluid reservoir toward the resilient chamber 604, and prevents a fluid from flowing toward the fluid reservoir through an inlet passage 616 of the resilient chamber 604 when pressure within the chamber is increased (e.g., when the resilient chamber 604 is compressed).

An inlet port 638 is coupled to the first end of the resilient chamber 604, and an outlet port 640 is coupled to the second end of the resilient chamber 604. Each of the inlet port 638 and the outlet port 640 comprise a first portion and a second portion. The inlet passage 616 extends through the first portion and second portion of the inlet port 638 and an outlet passage 618 extends through the first portion and second portion of the outlet port 640.

The first portion of the inlet port 638 and the outlet port 640 comprises an inner cylindrical wall surrounded by an outer cylindrical wall. The outer diameter of the inner cylindrical wall is less than an inner diameter of a tube such that the tube extends between the inner cylindrical wall and the outer cylindrical wall when coupled to the first portion. The second portion of the inlet port 638 and the outlet port 640 comprises and inner cylindrical wall surrounded by an outer cylindrical wall. The outer diameter of the inner cylindrical wall is less than an inner diameter of resilient chamber 604 cylinder walls such that the resilient chamber 604 extends between the inner cylindrical wall and the outer cylindrical wall when coupled to the second portion. A valve seat 668 extends around the inlet passage 616 at the second portion of the inlet port 638. The valve seat 668 has an inner cross-sectional width that is greater than or equal to the outer cross-sectional width of the check valve 606 retained within the valve seat 668.

In some embodiments the check valve 606 is retained in the valve seat by a cradle 650 having a fluid passage therethrough. In an embodiment, the cradle 650 is shaped as a cylinder having an open first end and an open second end with a ridge extending partially inward from the circumference of the cylinder. The open first end of the cradle 650 is affixed around the valve seat 668 such that the check valve 606 is retained between the valve seat and the ridge of the cradle 650.

The check valve 606 limits a fluid flow only a direction through the inlet port 638 toward the resilient chamber 604. When the resilient chamber 604 is compressed, pressure within the chamber is increased. The increased pressure drives the fluid out of the resilient chamber 604. Because there is a check valve 606 in the inlet port 638, the fluid is directed from the resilient chamber 604 through the outlet port 640.

The depth of the valve seat 669 at the outlet port 640 is greater than the depth of valve seat 668 at the inlet port 638. The greater valve seat 669 depth permits the check valve 644 to be installed in an orientation to permit a fluid flow only a direction from the resilient chamber 604 through the outlet port 640.

In some embodiments, the check valves 606 and 644 are a duckbilled check valve. However, the check valves 606 and 644 may be any type of valve that normally allows fluid to flow through the valve in only one direction, such as an umbrella valve or disk valve.

In operation, the inlet port 638 is fluidly coupled with a fluid reservoir (not shown) such that the inlet passage 616 is in fluid communication with the fluid reservoir. Fluid from the fluid reservoir begins to enter the resilient chamber 604 by passing through the inlet passage 616 and check valve 606. The fluid which initially begins to fill the resilient chamber 604 may contain both liquid and gas. To remove the gas, the fluid delivery system must be primed.

The fluid delivery system is primed by coupling the outlet port 640 with the fluid reservoir through tubing. To begin priming, the resilient chamber 604 is partially filled with the fluid. In some embodiments, the fluid is driven into the resilient chamber 604 by compressing the fluid reservoir. In some embodiments, fluid is drawn into the resilient chamber 604 by compressing and releasing the resilient chamber 604. As the compressed resilient chamber 604 returns to its neutral shape, fluid is drawn from the fluid reservoir into the resilient chamber 604. In either instance, the fluid passes through the check valve 606 as it enters the resilient chamber 604. Next, the resilient chamber 604 is compressed, thereby driving the liquid and gas through the outlet passage 618 of the resilient chamber 604. The liquid and gas are prevented, or impeded, from exiting the resilient chamber 604 through the inlet passage 616 by the check valve 606. The liquid and gas exiting the resilient chamber 604 through the outlet passage 618 are then directed from the outlet port 640 to the fluid reservoir through tubing.

As the resilient chamber 604 is repeatedly compressed and released, liquid from the fluid reservoir is drawn into the priming system and fluid, containing liquid and gas, is returned into the fluid reservoir. Once gas is no longer present in the fluid delivery system, or reduced to a satisfactory level, the tubing may be disconnected from the fluid reservoir and redirected to a catheter, pump, or other delivery device for delivery of the fluid to the patient.

Referring to FIGS. 17-21, an embodiment of a priming device is illustrated having a resilient chamber 704 and a check valve 706. The priming device includes a housing 702 having an inlet passage 716 and an outlet passage 718. The inlet passage 716 extends from an inlet port 738 to the resilient chamber 704, and is configured to receive a fluid from a fluid reservoir. An outlet passage 718 extends from the resilient chamber 704 to an outlet port 741 configured to direct a fluid away from the resilient chamber 704.

The check valve 706 is coupled to the inlet passage 716 between the fluid reservoir and the resilient chamber 704. The check valve 706 limits a fluid flow only a direction from the fluid reservoir toward the resilient chamber 704, and prevents a fluid from flowing toward the fluid reservoir through the inlet passage 716 when pressure within the resilient chamber 704 is increased (e.g. when the resilient chamber 704 is compressed).

The inlet port 738 and the outlet port 740 comprise an inner cylindrical wall surrounded by an outer cylindrical wall. The outer diameter of the inner cylindrical wall is less than an inner diameter of a tube such that the tube extends between the inner cylindrical wall and the outer cylindrical wall when coupled to the first portion.

A portion of the housing 702 comprises a planar surface forming a seat 734 for coupling of the resilient chamber 704 to the housing 702. The inlet passage 716 and the outlet passage 718 extend through and coaxially with the seat 734. A valve seat 768 and 769 is formed at the intersection of the inlet passage 716 and the outlet passage 718 with the seat 734, respectively.

The resilient chamber 704 is shaped as a cylinder having a domed portion and an opening opposite the domed portion. A flange 732 surrounds the opening and extends radially outward from the resilient chamber 704. The resilient chamber 704 comprises a resilient material such that the cylinder walls and domed portion will return to neutral shape after being expanded or compressed. The material and shape are selected such that after being deformed by compression, the resilient chamber 704 has sufficient expansive force to draw in fluid from a fluid reservoir coupled to the inlet port 738. In some embodiments, the material is the same as, or is structurally and/or functionally equivalent to that described above in embodiments depicted in FIGS. 2-8.

When the opening of the resilient chamber 704 is placed against the seat 734, the opening of the resilient chamber 704 is received and enclosed by the seat 734. A plane formed by the surface of the flange 732 is received within a ridge formed around the perimeter of the seat 734. The resilient chamber 704 is retained against the seat 734 by a circumferential retaining ring 736 which extends around the resilient chamber 704 and couples with the ridge portion of the seat 734. When the retaining ring 736 is coupled to the seat 734, the flange 732 is captured between the retaining ring 736 and seat 734 to form a fluid-tight seal.

In some embodiments, the outlet passage 718 includes a check valve 744, thereby limiting a fluid flow only a direction from the resilient chamber 704 toward the outlet port 740. When the resilient chamber 704 is compressed, pressure within the chamber is increased. The increased pressure drives the fluid out of the resilient chamber 704. Because there is a check valve 706 in the inlet port 738, the fluid is directed from the resilient chamber 704 through the outlet port 740. In some embodiments, the check valves 706 and 744 are duckbilled check valves. However, the check valves 706 and 744 may be any type of valve that normally allows fluid to flow through the valve in only one direction, such as an umbrella valve or disk valve.

In some embodiments, both the check valves 706 and 744 are retained within the valve seats 768 and 769 by a cradle 751 having a one or more fluid passage therethrough. The cradle 751 is shaped as a cup having an open first end and an open second end with a ridge extending partially inward from the second end of the cylinder. The open first end of the cradle 751 is then inserted into the valve seats 768 and 769 to retain the check valves 706 and 744. When affixed to the valve seats 768 and 769, the check valve 706 of the inlet passage 716 extends through the open second end of the cradle 751, while the check valve 744 of the outlet passage 718 away from the cradle 350. In some embodiments, each check valve 706 and 744 may be retained in the valve seats 768 and 769 by individual cradles 751.

In operation, the inlet port 738 is fluidly coupled with a fluid reservoir (not shown) such that the inlet passage 716 is in fluid communication with the fluid reservoir. Fluid from the fluid reservoir begins to enter the resilient chamber 704 by passing through the inlet passage 716 and the check valve 706. The fluid which initially begins to fill the resilient chamber 704 may contain both liquid and gas. To remove the gas, the fluid delivery system must be primed.

The fluid delivery system is primed by coupling the outlet port 740 with the fluid reservoir through tubing. To begin priming, the resilient chamber 704 must be at least partially filled with the fluid. In some embodiments, the fluid is driven into the resilient chamber 704 by compressing the fluid reservoir. In some embodiments, fluid is drawn into the resilient chamber 704 by compressing and releasing the resilient chamber 704. As the compressed resilient chamber 704 returns to its neutral shape, fluid is drawn from the fluid reservoir into the resilient chamber 704. In either instance, the fluid passes through the check valve 706 as it enters the resilient chamber 704. Next, the resilient chamber 704 is compressed, thereby driving the liquid and gas through the outlet passage 718 of the resilient chamber 704. The liquid and gas are prevented or impeded from exiting the resilient chamber 704 through the inlet passage 716 by the check valve 706. The liquid and gas exiting the resilient chamber 704 through the outlet passage 718 are then directed from the outlet port 740 to the fluid reservoir through tubing.

As the resilient chamber 704 is repeatedly compressed and released, liquid from the fluid reservoir is drawn into the priming system and fluid, containing liquid and gas, is returned into the fluid reservoir. Once gas is no longer present in the fluid delivery system, or reduced to a satisfactory level, the tubing may be disconnected from the fluid reservoir and redirected to a catheter, pump, or other delivery device for delivery of the fluid to the patient.

The foregoing description is provided to enable a person skilled in the art to practice the various configurations described herein. While the subject technology has been particularly described with reference to the various Figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A priming device comprising:
    a housing having a first fluid pathway and a second fluid pathway, a portion of the housing extending radially outward from an axis defined by a spike portion of the housing to form a base;
    a planar surface at an end of the base, the planar surface forming a seat disposed across an inner diameter of the base;
    an inlet port and an outlet port extending coaxially with the seat and extending through the seat;
    a resilient chamber coupled to the seat and having flexible walls, wherein the first fluid pathway and the second fluid pathway are fluidly coupled to the resilient chamber; and
    a first check valve in the first fluid pathway such that a fluid flow through the first check valve is only in a direction toward the resilient chamber,
    wherein compression of the flexible walls of the resilient chamber directs a fluid out of the resilient chamber and through the second fluid pathway.

2. The priming device of claim 1, wherein the housing comprises a drip chamber such that a fluid received into the first fluid pathway is driven through the drip chamber and the first check valve before entering into the resilient chamber.

3. The priming device of claim 2, wherein the flexible walls of the resilient chamber are expanded by the fluid driven into the resilient chamber.

4. The priming device of claim 1, wherein when not manually depressed, the flexible walls of the resilient chamber are configured to expand, and expansion of the flexible walls of the resilient chamber draws a fluid received through the first fluid pathway into the resilient chamber.

5. The priming device of claim 1, wherein the resilient chamber is hemispherically shaped.

6. The priming device of claim 5, wherein a retaining ring is coupled to the housing such that the resilient chamber extends through and is retained by the retaining ring.

7. The priming device of claim 1, wherein a second check valve is disposed in the second fluid pathway such that a fluid flow through the second check valve is only in a direction away from the resilient chamber.

8. The priming device of claim 1, wherein the first fluid pathway and the second fluid pathway each comprises an opening through the housing, each opening being juxtaposed through the spike portion of the housing.

9. The priming device of claim 1, wherein the inlet port comprises a needleless medical connector.

10. The priming device of claim 9, wherein the needleless medical connector comprises a flexible valve, wherein in a sealed position the flexible valve seals the inlet port, and in an open position, the flexible valve does not seal the inlet port.

11. A method of priming the priming device of claim 1, comprising the steps of:
    receiving a fluid into the first fluid pathway of the housing;
    directing the fluid through the first check valve in the first fluid pathway and into the resilient chamber; and
    manually compressing the flexible walls and directing the fluid through a second fluid pathway.

12. The method of claim 11, wherein directing the fluid into the resilient chamber causes the flexible walls to expand.

13. The method of claim 11, further comprising the step of directing the fluid through a second check valve in the second fluid pathway.

14. The method of claim 11, further comprising the step of receiving the fluid into the first fluid pathway from a fluid reservoir.

15. The method of claim 14, further comprising the step of directing the fluid from the second fluid pathway to the fluid reservoir.

16. The method of claim 14, further comprising the step of directing the fluid through a drip chamber coupled to the first fluid pathway between the fluid reservoir and the first check valve.

* * * * *